US012721748B2

(12) United States Patent
Werner et al.

(10) Patent No.: US 12,721,748 B2
(45) Date of Patent: Sep. 1, 2026

(54) HEATING DEVICE FOR PERFUSION FLUID, CHANNEL AND HEATING ASSEMBLY

(71) Applicants: ThermaSolutions LLC, White Bear Lake, MN (US); ThermaSolutions Europe B.V., Breda (NL)

(72) Inventors: Klaus Werner, Wijchen (NL); Stephan Holtrup, Erkelenz (DE); Anna Helena Ter Stege-Hake, Breda (NL)

(73) Assignees: ThermaSolutions LLC; ThermaSolutions Europe B.V., Breda (NL)

( * ) Notice: Subject to any disclaimer, the term of this patent is extended or adjusted under 35 U.S.C. 154(b) by 0 days.

(21) Appl. No.: 19/429,824

(22) Filed: Dec. 22, 2025

(65) Prior Publication Data

US 2026/0124069 A1 May 7, 2026

Related U.S. Application Data

(63) Continuation of application No. 19/113,345, filed as application No. PCT/NL2023/050448 on Aug. 31, 2023.

(30) Foreign Application Priority Data

Sep. 1, 2022 (NL) ..................................... 2032939

(51) Int. Cl.
*A61F 7/00* (2006.01)
*A61F 7/12* (2006.01)

(52) U.S. Cl.
CPC .... *A61F 7/0085* (2013.01); *A61F 2007/0072* (2013.01); *A61F 2007/126* (2013.01)

(58) Field of Classification Search
CPC ............ A61F 7/0085; A61F 2007/0072; A61F 2007/126; A61F 7/12; A61F 7/123
See application file for complete search history.

(56) References Cited

U.S. PATENT DOCUMENTS 5,931,865 A 8/1999 Silverman et al.
2019/0261654 A1 * 8/2019 Fine ......................... H05B 6/60

FOREIGN PATENT DOCUMENTS

DE 739925 C 10/1943
EP 0089242 A2 * 9/1983 .......... H10P 14/3411

(Continued)

OTHER PUBLICATIONS

International Search Report and Written Opinion Application No. PCT/NL2023/050448, dated May 12, 2023, 11 pages.

*Primary Examiner* — Sean W Collins
(74) *Attorney, Agent, or Firm* — AEON Law, PLLC; Adam L.K. Philipp; Charlotte E. Holoubek

(57) ABSTRACT

The invention relates to a heating device (100) for heating a fluid used in a medical procedure, comprising: a holder (110) arranged for receiving a channel (10) comprising a channel wall (11) arranged for conducting the fluid; and an electrical circuit (120) comprising: a first conductive surface (135), arranged to the holder for in use annularly surrounding the channel and together with the channel wall and the fluid forming a first capacitor (130) contributing to the capacitance of the electrical circuit, and for generating a first electrical field in the channel wall for introducing a first capacitively coupled current in the fluid; a second conductive surface (155), arranged to the holder for in use annularly surrounding the channel and together with the channel wall and the fluid forming a second capacitor (150) contributing to the capacitance of the electrical circuit, and for generating a second electrical field in the channel wall for introducing a second capacitively coupled current in the fluid; and an inductor (140) contributing to the inductance of the electrical circuit, and arranged to the holder for generating a magnetic field for introducing an inductively coupled current in the fluid; wherein the electrical circuit further comprises a connector (125, 125') electrically coupled to the first (Continued)

conductive surface, the second conductive surface and the inductor, and couplable to a power source providing a quasi-static AC power to the electrical circuit at an operating frequency.

20 Claims, 4 Drawing Sheets

(56) References Cited

FOREIGN PATENT DOCUMENTS

| | | | |
|---|---|---|---|
| WO | 9604805 | A1 | 2/1996 |
| WO | 2011062499 | A1 | 5/2011 |
| WO | 2012176194 | A1 | 12/2012 |
| WO | 2017205142 | A1 | 11/2017 |
| WO | 2020208345 | A1 | 10/2020 |

* cited by examiner

HEATING DEVICE FOR PERFUSION FLUID, CHANNEL AND HEATING ASSEMBLY

FIELD OF THE INVENTION

The invention relates to a heating device for heating a fluid used in a medical procedure. The invention further relates to a channel for use in a heating device. The invention further relates to a heating assembly comprising the heating device and the channel.

BACKGROUND OF THE INVENTION

Perfusion is a medical procedure where a fluid is passed through the circulatory system or lymphatic system to an organ or a tissue. Hyperthermic perfusion is a medical procedure, in which a warmed solution containing anticancer drugs, is used to bathe, or is passed through the blood vessels of, the tissue or organ containing the tumour.

A known solution providing a sterile heating of the perfusion fluid is to heat a primary fluid. The primary fluid is then passed through a heat exchanger together with the perfusion fluid to transfer the heat to the perfusion fluid. A disadvantage is that the temperature control of the perfusion fluid is coarse as well as slowly ramping up.

Another solution is to place a heating element inside the channel. A disadvantage of this solution is that local to the heating element the fluid can get very hot, such that local temperatures exceed some predefined temperature causing irreversible changes in the fluid, which typically contains medicines or proteins.

SUMMARY OF THE INVENTION

An object of the invention is to overcome one or more of the disadvantages mentioned above.

According to a first aspect of the invention, a heating device for heating a fluid used in a medical procedure, comprising: a holder arranged for receiving a channel comprising a channel wall arranged for conducting the fluid; and an electrical circuit comprising: a first conductive surface (135), arranged to the holder for in use annularly surrounding the channel and together with the channel wall and the fluid forming a first capacitor contributing to the capacitance of the electrical circuit, and for generating a first electrical field in the channel wall for introducing a first capacitively coupled current in the fluid; a second conductive surface (155), arranged to the holder for in use annularly surrounding the channel and together with the channel wall and the fluid forming a second capacitor (150) contributing to the capacitance of the electrical circuit, and for generating a second electrical field in the channel wall for introducing a second capacitively coupled current in the fluid; and an inductor contributing to the inductance of the electrical circuit, and arranged to the holder for generating a magnetic field for introducing an inductively coupled current in the fluid; wherein the electrical circuit further comprises a connector electrically coupled to the first conductive surface, the second conductive surface and the inductor, and couplable to a power source providing a quasi-static AC power to the electrical circuit at an operating frequency.

The holder is shaped for receiving the channel. The channel may have a particular shape for accommodating use in a medical room, such as an operating room. The channel may be couplable to tubing, conduits and/or ducts for guiding the fluid from and to the patient for forming a fluid circuit. The channel comprises a channel wall impermeable for the fluid and for guiding, conducting and/or carrying the fluid in a predefined direction. The holder may have a beaker shape. The heating device may comprise a housing forming the holder. The fluid may be a perfusion fluid, an infusion fluid, a transfusion fluid, blood, or any other fluid that might be used in a medical procedure.

The electric circuit comprises a first conductive surface for forming in use a first capacitor, and an inductor. The electrical circuit further comprises a connector. The connector is electrically coupled to the first conductive surface and the inductor, such that when the connector is coupled to a power source providing power, the first conductive surface and the inductor are provided with this power from the power source. The power from the power source is quasi-static AC power. AC is short for alternating current. Quasi-static limits the frequencies provided by the power source to the electrical circuit. Quasi-static may be Galilean electromagnetism. Quasi-static may be considered as local equilibrium thermodynamics. Quasi-static are typically frequencies of which the wavelength of the AC power is larger than the size of the heating device, such as twice, preferably five times, more preferably ten times, most preferably twenty times. Quasi-static AC power typically means that the wave properties or wave propagation effects inside the heating device may be neglected or are neglectable when modelling the circuit, when modelling the working of the heating device, and/or when predicting efficiency and/or effects of the heating device, more specific the electrical circuit.

The first capacitor comprises a first conductive surface. The first conductive surface is arranged to the holder for generating a first electrical field in the channel wall. A first capacitor is therefore formed between the first conductive surface on one side of the channel wall and the fluid on the opposite side of the channel wall. The changing polarity of the first conductive surface due to the AC power will induce or introduce a displacement current in the fluid opposite the first conductive surface, which in turn will cause a first capacitively coupled current in the fluid. The fluid has a specific resistivity or specific conductivity per volume. The capacitively coupled current in the fluid towards and away from the first conductive surface will cause this capacitively coupled current to undergo the fluid resistivity. The alternating capacitively coupled current under the influence of the fluid resistivity will be transformed to heat in the fluid.

The inductor is arranged to the holder for generating a magnetic field for introducing an inductively coupled current in the fluid. The inductively coupled current in the fluid typically is an eddy current. Comparably to the first capacitively coupled current, the inductively coupled current will undergo the fluid resistivity. The alternating inductively coupled current under the influence of the fluid resistivity will be transformed to heat in the fluid.

Both the first capacitor and the inductor contribute to heating the fluid advantageously optimizing the use of the power source. Furthermore, the electrical circuit may comprise capacitance and inductance for advantageously reducing the reactance of the electrical circuit. Furthermore, as the heating device heats the fluid directly, the heating device provides a fine control over the temperature of the fluid. Furthermore, the absence of contact between the heating device and the fluid in the channel advantageously allows for sterilely heating the fluid in the channel. The capacitively coupled current and/or the inductively coupled current in the fluid are spread over a relatively large volume providing a more even heating of the fluid without locally exceeding a predefined temperature causing irreversible changes in the fluid, which typically contains medicines or proteins. The irreversible change typically causes solidification and/or disintegration of a particular portion or fraction of the fluid. The solidified fraction may cause clogging of parts of the fluid system or even in the patient. The disintegration of a particular portion or fraction of the fluid may cause the fluid to lose at least partly its function. Hence, the technical effect is that the heating device reduces clogging in the fluid system and/or the fluid retains its function.

The second capacitively coupled current may advantageously relate to the first capacitively coupled current for forming a closed electrical circuit. The channel typically is elongated defining an elongated axis. The first and the second capacitively coupled currents are substantially along the elongated axis. The first and the second capacitively coupled currents may therefore be typed as elongated currents or axial currents. These first and the second capacitively coupled currents have the tendency to spread out over the cross-section perpendicular to the elongated axis of the channel. The first and the second capacitively coupled currents generate the heat predominantly through these currents experiencing the fluid resistance. As these currents are spread out over the cross-section of the elongated channel, the heat generation is distributed over the cross-section of the channel. This evenly spreading out over the cross-section of the channel prevents or at least reduces the forming of hot spots thereby reducing the chance of clogging.

According to another aspect, a channel for use in a heating device according to any of the embodiments. The channel provides the advantages also provided by the heating device.

According to another aspect, a heating assembly comprising: a heating device according to any of the embodiments; and a channel according to any of the embodiments and for use in the heating device. The heating assembly provides the advantages also provided by the heating device.

According to another aspect, a flow sensor for measuring the flow of a fluid in a conduit, comprising: a heating device according to any of the embodiments; a first temperature sensor arranged upstream of the heating device for measuring the temperature of the fluid going into the heating device; a second temperature sensor arranged downstream of the heating device for measuring the temperature of the fluid coming from the heating device; and an electrical power sensor arranged for measuring the electrical power inputted into the fluid by the heating device; and a controller arranged for: receiving a first temperature from the first temperature sensor; receiving a second temperature from the second temperature sensor; receiving an electrical power value representing the electrical power inputted into the fluid; retrieving the thermal capacity of the fluid; retrieving the volumetric mass density of the fluid; and calculating the flow of the fluid based on the first temperature, the second temperature, the electrical power value, the thermal capacity, and the volumetric mass density. The heating device provides very accurate means for controlling the amount of heat energy inputted in the fluid. The flow sensor therefore has a high accuracy. The accuracy of the flow sensor typically depends on the accuracy of the temperature sensors and the electrical power value. Furthermore, the flow sensor provides a means of accurately controlling the amount of fluid flowing through the heating device and at the same time heating the fluid to an accurate temperature advantageously providing accuracy and/or compact design.

According to another aspect, a temperature sensor for sensing the temperature of a fluid, comprising: a heating device according to any of the embodiments mentioned in the description, wherein the fluid is conducted in the channel; a power source providing a quasi-static AC power to the electrical circuit of the heating device, comprising: a supply circuit for generating the operating frequency at a power output; and a sensor for detecting the impedance of the electrical circuit; and a controller arranged for: retrieving a function relating temperature and resonance frequency of the fluid; determining the resonance frequency of the fluid in the channel based on changing the operating frequency; and determining the fluid temperature of the fluid in the channel based on the resonance frequency and the function relating temperature and resonance frequency. The resonance frequency of the fluid typically changes with a change of temperature of the fluid. This relation is advantageously applied in the temperature sensor. The temperature sensor determines the resonance frequency bases on the measurements of the impedance sensor.

These measurements may be done with a high degree of accuracy. These measurements may also be statistically processed to enhance the accuracy of the determined resonance frequency. The temperature sensor therefore provides a relatively simple temperature measurement with high accuracy.

DETAILED DESCRIPTION OF EXEMPLARY EMBODIMENTS

In an embodiment of the heating device, the channel has a channel diameter and a longitudinal axis. The distance between the first conductive surface and the second conductive surface along the longitudinal axis typically is at least 1.0 times, preferably 1.5 times, more preferably 2.0, even more preferably 2.5, most preferably 3.0, the channel diameter. The distance between the first conductive surface and the second conductive surface along the longitudinal axis typically is at most 15 times, preferably 10 times, more preferably 5, even more preferably 4, most preferably 3, the channel diameter. These dimensions are typical for providing the axial currents.

In an embodiment of the heating device, the first conductive surface and the second conductive surface are arranged such that respectively the first capacitively coupled current in the fluid is substantially a first axial current and the second capacitively coupled current in the fluid is substantially a second axial current. This embodiment advantageously stipulates the direction of the capacitively coupled currents.

In an embodiment of the heating device, the first conductive surface has a first truncated conical inner shape; the second conductive surface has a second truncated conical inner shape; and the channel wall has at least partly a truncated conical shape for cooperating with the first conductive surface and the second conductive surface. The truncated conical shapes cooperating with the at least partly truncated conical shaped channel wall allows the channel wall to snugly fit into the annular conductive surfaces for reducing, minimizing, or even preventing an air gap between the respective conductive surface and the channel wall. An air gap, especially a small air gap causes high voltages over the air gap thereby possibly causing heating to build up on the surface of, around and/or in the channel wall to such an extend that carbonizing of the channel wall or sparking in the proximity of the channel wall may occur. Minimizing the air gap advantageously reduced these issues. Furthermore, a changing air gap cause a change in resonance frequency influencing the efficiency of the heating device. Minimizing or even preventing the air gap improves the stability of the resonance frequency and as a result advantageously stabilizes the efficiency of the heating device.

In an embodiment of the heating device, the inductor has also an inner truncated conical shape; and the channel wall has at least partly a truncated conical shape for cooperating with the inner shape of the conductor. The inductor snugly fitting around the channel wall prevents or at least limits the magnetic field outside the channel. Limiting or preventing the magnetic field outside the channel wall advantageously provides a more stable resonance frequency and more stable efficiency of the energy transfer by the inductor.

In an embodiment of the heating device, the first truncated conical shape has a minimum diameter; the second truncated conical shape has a maximum diameter; and the minimum diameter is larger than the maximum diameter. The removeable channel may be inserted in the heating device by inserting the channel into the first truncated conical shaped conductive surface towards the second truncated conical shaped conductive surface. This allows the channel to be easily insertable from one side of the heating device while still snugly fitting into the respective truncated conical shaped conductive surfaces for advantageously minimizing or at least controlling the air gap.

In an embodiment of the heating device, the first truncated conical shape and the second truncated conical shape are aligned to form one virtual conical shape. This advantageously gives a single truncated conical shaped channel over the complete length of the channel between the conductive surfaces. Preferably the inductor has also an inner truncated conical shape aligned with the respective truncated conical shapes of the conductive surfaces. This provides the advantage of a simple shape to the channel, which becomes easier to produce. Further, an aspect of the invention may be a channel shaped to cooperate with the holder. This channel is at least truncated conically shaped at the part cooperating with the first conductive surface, the second conductive surface, and the inductor. More preferably the channel is truncated conically shaped over the length of the channel fitting in and between the first and the second conductive surface.

In an embodiment of the heating device, the electrical circuit comprises the first conductive surface for forming in use the first capacitor, and the inductor. This embodiment advantageously heats the fluid with the capacitively coupled current and the inductively coupled current in the fluid. As both of the currents heat the fluid, both of the energies are advantageously used for 50 heating for increasing the efficiency as well as shortening the time needed for heating a volume of fluid in the channel. This embodiment may advantageously increase the fluid throughput in the channel as the heating time for heating a volume of the fluid is shortened. Alternatively, the fluid may be heated to a higher temperature due to the increased efficiency. Alternatively, the power inputted in the heating device may be minimized. In general, the power inputted into the heating device is preferably limited to the power from a wall socket in the US and/or Europe, typically a one phased wall socket.

In an embodiment of the heating device, the inductor is arranged for surrounding the channel. As the inductor is arranged around the channel, the magnetic field is advantageously easily introduced in the fluid for inducing the inductively coupled current for heating the fluid.

In a further embodiment of the heating device, the holder is arranged for a channel shaped to conduct the fluid an even number of times, preferably twice, through the magnetic field and/or the first capacitively coupled current. Having an even number of passes provides the advantage of having the input of the channel and the output of the channel at the same side of the holder.

The holder may be in the form of a cup shape for easily placing the channel in the holder. Furthermore, the channel may be coupled and/or decoupled to the rest of the fluid system and/or ducts away from the holder and/or the heating device advantageously preventing spilling in and/or contamination introduced in the fluid system by the holder and/or the heating device.

In a further embodiment of the heating device, the holder is arranged for a channel shaped to conduct the fluid an uneven number of times, preferably once, through the magnetic field and/or the first capacitively coupled current. This embodiment may provide the advantage of feeding the fluid through the magnetic field and/or the first capacitively coupled current. The preferred embodiment of carrying the fluid once through the magnetic field and/or the first capacitively coupled current provides a very simple embodiment of the channel.

In an embodiment of the heating device, the channel comprises an input opening and an output opening; and the input opening and the output opening are arranged on the same side of the magnetic field, the inductor, the first electric field, the second electric field, the first conductive surface and/or the second conductive surface. The holder may be in the form of a cup shape for easily placing the channel in the holder. Furthermore, the channel may be coupled and/or decoupled to the rest of the fluid system and/or ducts away from the holder and/or the heating device advantageously preventing spilling and/or contamination of the holder and/or the heating device.

In an embodiment of the heating device, the second capacitively coupled current advantageously matches the first capacitively coupled current for introducing a capacitively coupled current in the fluid between the first conductive surface and the second conductive surface. The matching of the two currents prevents the use of a ground electrode in contact with the fluid. The absence of the ground or return electrode in contact with the fluid prevents contamination of the fluid via the ground electrode. Furthermore, the absence of the ground electrode in contact with the fluid provides the advantage that the channel and the heating device, specifically the electrical circuit, don't have to be electrically conductively coupled, such as with a conductive wire, for advantageously simplifying the replaceability of the channel in the holder and/or advantageously simplifying the construction of the heating device and/or channel. The absence of the ground electrode in contact with the fluid may simplify the construction of the channel. In absence of a second conductive surface generating a second capacitively coupled current matching the first capacitively coupled current typically a ground electrode is used to close the electrical circuit. Introducing the second conductive surface and matching the capacitively coupled currents provides the advantage of halving the respective electrical fields in the two formed capacitors that are effectively coupled in series. Halving the respective electrical fields provides the advantage that the electrical field in the channel wall is reduced, such as halved, for advantageously limiting the heating of the channel wall.

In an embodiment of the heating device, the first conductive surface and the second conductive surface are arranged on either side of the inductor, such that the first capacitively coupled current and the second capacitively coupled current flow through the magnetic field. The first capacitively coupled current and the second capacitively coupled current flow through the fluid for a relatively long length such that the fluid provides the necessary resistance for generating heat from the current flowing through this fluid and thus resistance. Arranging the inductor between the first conductive surface and the second conductive surface advantageously provides a compact design of the heating device.

In a further embodiment of the heating device, the inductor is split in a first half and a second half; the first half of the inductor and the second half of the inductor are electrically coupled to the connector; the other side of the first half of the conductor is electrically coupled to the first conductive surface; and the other side of the second half of the conductor is electrically coupled to the second conductive surface. The provided electrical circuit is advantageously balanced such that a differential signal may be applied. The voltages over the channel wall introduced by the formed capacitors are advantageously reduced, such as halved.

Further, the currents introduced in the channel wall at the inductors are advantageously reduced, such as halved. The differential signal advantageously allows to limit, such as half, the amplitudes of the signals. Reducing the voltages over the channel wall reduces the heat development in and around the channel wall, or even carbonizing of the channel wall or sparking in the proximity of the channel wall.

In a further embodiment of the heating device, in use the fluid has a resistivity per volume; the first conductive surface and the second conductive surface are spaced apart a coupling distance; and the coupling distance is selected such that the fluid resistivity between the first conductive surface and the second conductive surface substantially matches the output resistivity of the power source. The resistance of the formed first capacitor, the formed second capacitor, and/or the inductor may be neglected relative to the fluid resistivity. For the transfer of power from a power source to the fluid, the resistivity of the heating device should match the resistance of the power source. The dominant resistance of the heating device is preferably the fluid resistivity. The fluid resistivity is determined by the width of the part of the channel conducting the current and the length of the part of the channel conducting the current herewith labelled coupling distance. For an example of heating a fluid, it was found that the capacitively coupled current experience the dominant fluid resistivity, while the inductively coupled current experiences the minor, less or even neglectable fluid resistivity. The heating device, preferably the fluid resistivity, is typically in the range of 5 Ohm to 500 Ohm, more preferably 20 Ohm to 100 Ohm, more preferably 40 Ohm to 60 Ohm, most preferably substantially 50 Ohm.

It may be noted that the fluid resistivity typically is temperature dependent. As the heating device heats the fluid, the fluid resistivity may change. Preferably, the change in fluid resistivity is such that the efficiency drops not considerably or the mismatch is not too high. The mismatch is preferably compensated with a power source adapting its output power resistance. In an embodiment, the fluid resistivity may be adapted, such as by changing the distance, labelled coupling distance, between the formed first and the formed second capacitor.

The heating of the fluid may influence the resonance frequency of the heating device. The resonance peak may for the application of heating fluids be 20-30 kHz. A shift of this peak due to heating may cause the heating device to lose resonance and become highly inefficient. The power source preferably adapts its supply frequency to the current resonance frequency and/or operating frequency of the heating device for optimizing the efficiency of the heating device.

In an embodiment of the heating device, in use the channel wall at the first conductive surface has a first relative permittivity; in use the first capacitor has a first capacitance depending on the first relative permittivity and thickness of the channel wall local to the first conductive surface; in use the fluid has a magnetic permeability; the inductance is based on the magnetic permeability of the fluid; the electrical circuit has a resistance based on the resistivity of the first capacitively coupled current, the inductively coupled current; the electrical circuit has a reactance based on the capacitance and the inductance; and at the operating frequency, the ratio of the resistance and reactance is more 2:1, preferably 5:1, more preferably 10:1, most preferably 20:1. In an extended embodiment, in use the channel wall at the second conductive surface has a second relative permittivity; in use the second capacitor has a second capacitance depending on the second relative permittivity and thickness of the channel wall local to the second conductive surface; the electrical circuit also has a resistance based on the second capacitively coupled current. As the reactance is low compared to the resistance, the resistance, typically the fluid resistance, is dominant over the reactance, and thus, the heat device advantageously mainly generates heat through the dominant resistance in the fluid.

Alternatively, the electrical circuit in use has a reactance based on the capacitive reactance from the first capacitor and the second capacitor, and the inductive reactance from the inductor. The resulting reactance may be the addition of the capacitive reactance and the inductive reactance, wherein the capacitive reactance and the inductive reactance have opposite effects. The capacitive reactance and the inductive reactance substantially cancel each other out. Preferably, the resulting reactance compared to the capacitive reactance as well as the inductive reactance is small, such as 1:5, preferably 1:10, more preferably 1:50, most preferably 1:100.

In an embodiment of the heating device, the operating frequency is below 450 MHz, preferably within the range of 1 MHz to 100 MHz, more preferably within the range of 5 MHz to 60 MHz, more preferably within the range of 10 MHz to 40 MHz, even more preferably within the range of 20 MHz to 35 MHz, most preferably substantially 27 MHz. The frequencies are selected such that the quasi-static AC power requirement is fulfilled with a reasonable sized heating device, specifically holder and subsequent channel size or length.

The operating frequency is preferably selected at a frequency which may be freely used in a particular country simplifying use, more specific typically licensing. The operating frequency is within the range of 433.05 MHz to 434.79 MHz. The operating frequency is within the range of 40.66 MHz to 40.7 MHz. The operating frequency is within the range of 26.957 MHz to 27.283 MHz. The operating frequency is within the range of 13.553 MHz to 13.567 MHz. The operating frequency is within the range of 6.765 to 6.795 MHz.

In an embodiment of the heating device, in use the electrical circuit has a Q-factor based on the resistance, the capacitance, and the inductance; the Q-factor is selected to accommodate for changes of the relative permittivity of the fluid and/or the magnetic permeability of the fluid over the temperature range of the fluid, and/or for changes of the relative permittivity of the fluid and/or the magnetic permeability of the fluid over different production batches. In a further embodiment, the Q-factor is selected in the range of 0.2-12, preferably in the range of 0.4-8, more preferably 1.0-6, more preferably 2-4, most preferably around 3. The resistance of the capacitively coupled current may be influenced by changing the length of the fluid volume conducting this current, and/or the cross-sectional area of the fluid conducting this current. The resistance of the inductively coupled current may be influenced by changing the cross-sectional fluid area exposed to the magnetic field of the inductor, such as enveloped by the inductor. The capacitance may be influenced by introducing and/or changing an airgap between the first conductive surface and the channel, and/or the second conductive surface and the channel. The capacitance may be influenced by changing the wall thickness of the channel whereover the first and/or the second conductive surface is arranged. The inductance may be influenced by changing the number of windings of the inductor comprising a coil. The inductance may be influenced by changing the area enclosed by the inductor comprising a coil.

In a further embodiment of the heating device, the Q-factor is selected to accommodate in use for an air gap between the channel wall and the first conductive surface, and the channel wall and the second conductive surface, of up to 100 μm, preferably 50 μm, more preferably 25 μm, most preferably 15 μm. In a preferred embodiment, the holder is a receptacle providing the advantage of collecting any spillage of for example the heated fluid and/or any body fluids. A relatively small channel wall allowing air into the holder, specifically the receptacle, allows for easily removing the channel from the holder without e.g. drawing a vacuum or under pressure between channel and holder.

In a further embodiment of the heating device, the heating device comprises a reactance sensor for sensing a reactance, preferably the capacitance, of the electric circuit relative to a predefined reactance range, preferably a predefined capacitance range, for detecting the presence of a channel in the holder, the correct placing of the channel in the holder, the filling degree of the channel with fluid, and/or if the correct fluid is in the channel. This reactance sensor provides the advantage of a simple and straight forward method for detecting the presence of the channel in the holder, detecting if the channel is correctly placed in the holder, detecting if the correct channel is located in the holder, and/or detecting if the correct fluid is present in the channel. In summary, the reactance sensor may be arranged for advantageously functionally checking the functioning of the heating device.

In a further embodiment, the heating device comprises a setting for setting the reactance such that different channels may differentiated and used in the heating device. This setting may also be used to heat the fluid to different temperatures. The setting may also determine or influence the operating frequency of the heating device. The different channels may uniquely identify the channel for use for a specific medical procedure or at least some or all of the settings of the heating device. The setting provides the advantage of improved failsafe of use of the heating device for different medical procedures.

In an embodiment of the heating device, the heating device is arranged for heating the fluid up typically under atmospheric pressure to a maximum temperature of 55 degrees Celsius, preferably 50 degrees Celsius, most preferably 45 degrees Celsius. The temperature may advantageously be selected such that when the fluid, such as a perfusion fluid, a transfusion fluid or infusion fluid, enters the body during a medical procedure that the fluid has the temperature necessary for that medical procedure. The fluid may be used for a medical procedure wherein due to the temperature of the fluid necrosis of cancer cells is triggered while at least most healthy cells aren't triggered to set in necrosis.

In an embodiment of the heating device, the fluid is heated up typically under atmospheric pressure to a temperature. The temperature may advantageously be selected such that, when the fluid for example is blood or any other fluid holding proteins, the fluid has the temperature necessary for that medical procedure. As a further example, blood or any other protein holding fluid may be taken from a cooling storage and should be brought into the blood system of a patient. If the temperature of the fluid brought into the blood system is too low, the patient may cooldown and may even go into shock. If the temperature of the fluid brought into the blood system is too high, the proteins in fluid may at least partly decompose or disintegrate, losing its function at least partly. Specifically mentioned is the temperature of around 56 degrees Celsius, being the temperature for denaturalization of protein, typically present in blood or blood products. The current heating device is arranged for evenly heating the fluid in the channel preventing local overheating while still providing an overall desired temperature to the fluid.

In an embodiment of the heating device, the holder is arranged for replacing the channel. The replaceable channel provides the advantage of ease of use for example for different medical procedures or patients.

In an embodiment of the heating device, the channel has an outer channel shape; and the holder has a tapered shape for receiving a tapered outer channel shape. This embodiment advantageously provides ease of replacing the channel in the holder.

The channel almost automatically slides to the right position tightly pressing the channel wall preferably onto the first conductive surface and/or the second conductive surface. Furthermore, the channel wall may be pressed onto the inductor for preventing an air gap.

In an embodiment of the heating device, in use the fluid has a magnetic permeability; in use the channel has a magnetic permeability; and the electric circuit is arranged for a fluid and a channel wherein the channel magnetic permeability is neglectable compared to the fluid magnetic permeability, such as in a ratio of 1:5, preferably 1:10, more preferably 1:15, even more preferably 1:20.

In an embodiment of the heating device, in use the fluid has a relative permittivity; in use the channel has a relative permittivity; and the electric circuit is arranged for a fluid and a channel wherein the fluid relative permittivity is neglectable compared to the channel relative permittivity, such as in a ratio of 1:25, preferably 1:35, more preferably 1:40, even more preferably 1:50. Ratio of PP to water is approximately 2.4/78 which is about 1:33. Another ratio may be PTFE relative to water which is 2.1/78 which is about 0.0269 or ⅓8.

In an embodiment of the heating device, in use the fluid is a perfusion fluid, a transfusion fluid or an infusion fluid. The heating device provides the advantage of controlled and quick heating of the fluid, such that the fluid may be used for perfusion, such as perfusion in a medical procedure, a transfusion fluid, such as transfusion in a medical procedure or infusion, such as infusion in a medical procedure. The perfusion fluid may be used in a medical procedure for triggering necrosis in cancer cells in tissue of a patient. The infusion fluid may be used in a medical procedure for replacing or supplementing fluids in a body. The transfusion fluid may be used in a medical procedure for adding or supplementing fluids, such as blood, in a body. The control and short time for heating makes the heating device highly useable for this type of medical procedure.

In an embodiment of the channel, the channel is shaped to fit, preferably snugly fit, in the holder for minimizing the airgap between the channel and at least one of the group of the first conductive surface, the inductor, and the second conductive surface. The channel and the holder are preferably tapered in shape such that the air gap is minimized by snugly and easily fit together the channel and at least one of the group.

In an embodiment of the channel, the channel comprises a first flexible section arrangeable to the first conductive surface for cooperating with the first conductive surface; and/or a second flexible section arrangeable to the second conductive surface for cooperating with the second conductive surface. The flexible section, preferably sections, advantageously adapt to the shape of the respective conductive surfaces, such that an air gap between conductive surface and channel is minimized or even prevented.

Further, the flexible section advantageously allows to easily exchange the channel. The flexible section may be seen as liner arrangeable to the conductive surface.

In a further embodiment of the channel, the first flexible section has a truncated conical shaped for cooperating with the first truncated conical inner shape of the first conductive surface; and the second flexible section has a truncated conical shaped for cooperating with the second truncated conical inner shape of the second conductive surface. The flexible section, preferably sections, being pre-shaped in a truncated conical shape advantageously allows the flexible sections to better adapt to the truncated conical shaped conductive surfaces.

In a further embodiment of the channel, the channel has a width in the range of 20-100 mm, preferably 30-80 mm, more preferably 40-60 mm, most preferably around 50 mm.

In an embodiment of the heating device, the channel wall comprises a wall material for providing a relative magnetic permeability in the range of relative magnetic permeability in the range of 0.3-2.0, preferably 0.6-1.5, more preferably 0.8-1.2, most preferably 0.9-1.1 and/or a relative permittivity in the range of 1-11, more preferably 2-10, most preferably 2-4, such as for plastics, or 9-10, such as for ceramics; and the wall material is preferably selected from or combinations of Polytetrafluorethylene (PTFE), Polyethyleen (PE), Polypropyleen (PP), Cyclisch olefinic copolymeer (COC), Polymethylterpenteen (TPX), and Polystyreen (PS).

In a further embodiment of the heating assembly, the heating assembly comprises a power source for powering the electrical circuit of the heating device. The quasi-static AC power condition provides the advantage that wave guidance may be ignored for estimating the resonance frequency for advantageously coming to a relatively simple design of the heating device. The quasi-static AC power condition provides the advantage that parasitic high frequency effects may be neglected. Furthermore, the quasi-static AC power condition advantageously provides a reduction of radiation of the AC power supplied to the heating device.

In a further embodiment of the heating assembly, the power source comprises: a supply circuit for generating the operating frequency; and a sensor for detecting the impedance of the electrical circuit; and wherein the power source changes the operating frequency towards the resonance frequency of the electrical circuit based on the sensor measurement. The resonance frequency may change during heating of the fluid in the channel. Also, the resonance frequency may change from batch to batch of channels used and fluid used due to production variations. The heating assembly advantageously optimizes the energy transfer from the power source to the heating device and eventually into the to be heated fluid while heating and/or due to production variations.

In a further embodiment of the heating assembly, the power source comprises a matchbox arranged for minimizing the reactance of the electrical circuit at the operating frequency. This advantageously optimizes the energy transfer between power source and the heating device, more specifically the fluid in the channel.

In a further embodiment of the heating assembly, the matchbox comprises a variable impedance for adapting the impedance of the electrical circuit; and the matchbox changes the variable impedance based on the sensor measurement such that the impedance of the matchbox and the electrical circuit matches the impedance of the power source, the reactance of the matchbox and the electrical circuit matches the impedance of the power source, and/or the resistance of the matchbox and the electrical circuit matches the impedance of the power source. This advantageously further optimizes the energy transfer between power source and the heating device, more specifically the fluid in the channel.

In an embodiment of the heating assembly, the heating assembly is combined with any of the features introduced in any of the other embodiments, particularly the embodiments of the heating device, for obtaining the same advantages as mentioned for that particular embodiment.

In a further embodiment of the flow sensor, the step of calculating comprises the steps of: subtracting the first temperature from the second temperature for providing a temperature change; determining a received energy value based on the heat capacity and the temperature change; dividing the electrical power value by the received energy for providing the mass per time unit of the flow; dividing the mass of the flow by the volumetric mass density for providing the volume per time unit of the flow. This embodiment advantageously details the calculation step.

In a further embodiment of the flow sensor, the flow sensor comprises a first pressure sensor arranged for measuring the pressure of the fluid at the first temperature sensor; and a second pressure sensor arranged for measuring the pressure of the fluid at the second temperature sensor; wherein the step of determining is based on the pressure measurement of the first pressure sensor and the pressure measurement of the second sensor, more specific on the pressure difference of the fluid at the first temperature sensor and at the second temperature sensor. This embodiment advantageously details the determining step, specifically taking into account the change of pressure due to the heating of the fluid.

In an embodiment of the flow sensor, at least one of the heating devices in the flow sensor is combined with any of the features introduced in any of the other embodiments, particularly the embodiments of the heating device, for obtaining the same advantages as mentioned for that particular embodiment.

In an embodiment of the temperature sensor, the step of determining the resonance frequency comprises: changing the operating frequency over a frequency range; receiving impedance measurements, measured while changing the operating frequency, from the impedance sensor for detecting the impedance; and determining the resonance frequency based on the operating frequency with the lowest impedance. The changing of the operating frequency may be a frequency sweep. The changing of the operating frequency may behave like a damped resonance around the resonance frequency for gradually approaching the resonance frequency. Interpolation may be used around the operating frequency with the lowest impedance for enhancing the accuracy of the determined resonance frequency. Multiple measurements at the same operating frequency may be used to statistically enhance determining the resonance frequency. In a preferred embodiment, multiple measurements at the same operating frequency and interpolation for further enhancing the accuracy of the determined resonance frequency.

In an embodiment of the temperature sensor, the controller is arranged for minimizing the power output of the supply circuit at least during determining the resonance frequency, preferably during changing the operating frequency. Minimizing the power output provides the advantage that the fluid in the channel does not significantly change temperature or at least the temperature change of the fluid in the channel is minimized. For the minimal power output, a balance is to be found between noise becoming dominant at low power output settings influencing the accuracy of the temperature measurement and the fluid temperature changing during the measurement of the temperature.

In an embodiment of the temperature sensor, the controller is arranged for: receiving a required fluid temperature; and setting the power output for heating the fluid to the required fluid temperature based on the required fluid temperature. This advantageously combines measuring the fluid temperature and heating the fluid in the channel. The fluid temperature flowing out of the channel may be controlled by advantageously combining the temperature sensor function with the heating device function.

The fluid temperature flowing out of the channel may follow a specific temperature profile, such as a continues temperature or ramping up.

In an embodiment of the temperature sensor, setting the power output is also based on one or more determined fluid temperatures. This embodiment specifies closing a control loop, such may be done with a PID controller, fuzzy logic, or the like, for controlling the fluid temperature flowing out of the channel. A fluctuating temperature of the fluid flowing into the channel has less influence or a reduced influence on the fluid temperature of the fluid flowing out of the channel. Furthermore, the dimensions of the channel do not have to be predetermined for this embodiment, as the fluid temperature flowing out of the channel is measured and controlled in this embodiment.

In an embodiment of the temperature sensor, the heating device in the temperature sensor is combined with any of the features introduced in any of the other embodiments, particularly the embodiments of the heating device, for obtaining the same advantages as mentioned for that particular embodiment.

BRIEF DESCRIPTION OF THE DRAWINGS

The invention will be apparent from and elucidated further with reference to the embodiments described by way of example in the following description and with reference to the accompanying drawings, in which.

LIST OF REFERENCE NUMERALS

Figure 2:
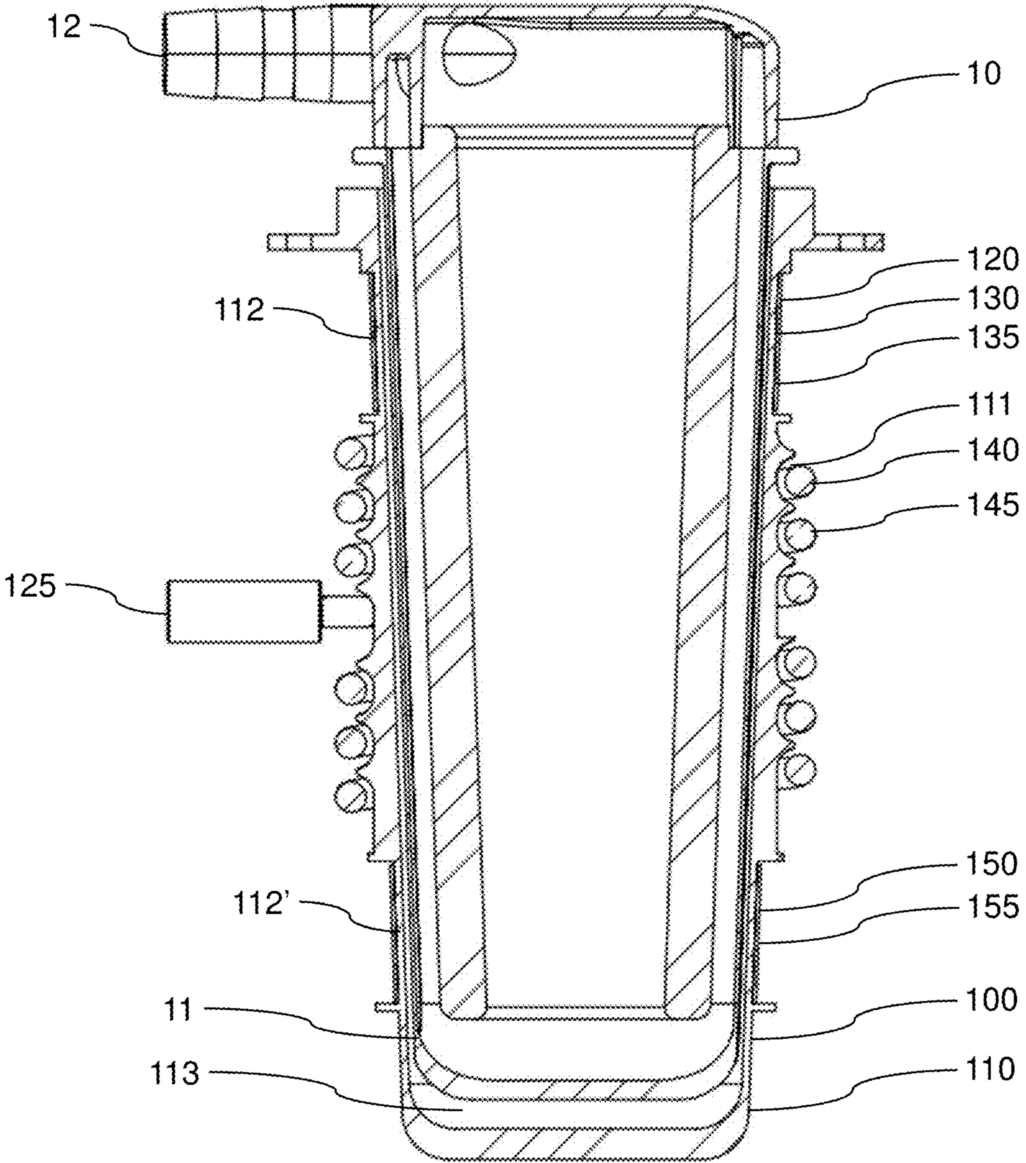
FIG. 2 schematically shows a cross-section of a heating device.

| | |
|---|---|
| 10 | channel |
| 11 | channel wall |
| 12 | fluid inlet |
| 13 | fluid outlet |
| Rs1, Rs2, Rs3, Rs4, Rs5, LOAD1 | fluid resistance |
| 100 | heating device |
| 110 | holder |
| 111 | grooves |
| 112, 112' | recess |
| 113 | beaker space |
| 120 | electrical circuit |
| 125, 125' | electrical connector |
| Rw/2, Rw/2' | resistors |
| Cl, Cl', Cl'', Cl''' | parasitic capacitor |
| Ls/2, Ls/2' | parasitic inductor |
| 130, CM1, C1 | first capacitor |
| 131 | first capacitor connector |
| 135 | first conductive surface |
| 140, L1 | inductor |
| 145 | inductor winding |
| 146, Lh/2 | upper inductor half |
| 147, Lh/2' | lower inductor half |
| 150, CM2 | second capacitor |
| 151 | second capacitor connector |
| 155 | second conductive surface |
| CTUNE1 | capacitive matchbox |
| LTUNE1 | inductive matchbox |
| A | cross-section shown in FIG. 2 |

DETAILED DESCRIPTION OF THE FIGURES

The following figures may detail different embodiments. Embodiments can be combined to reach an enhanced or improved technical effect. These combined embodiments may be mentioned explicitly throughout the text, may be hint upon in the text or may be implicit.

Figure 1:
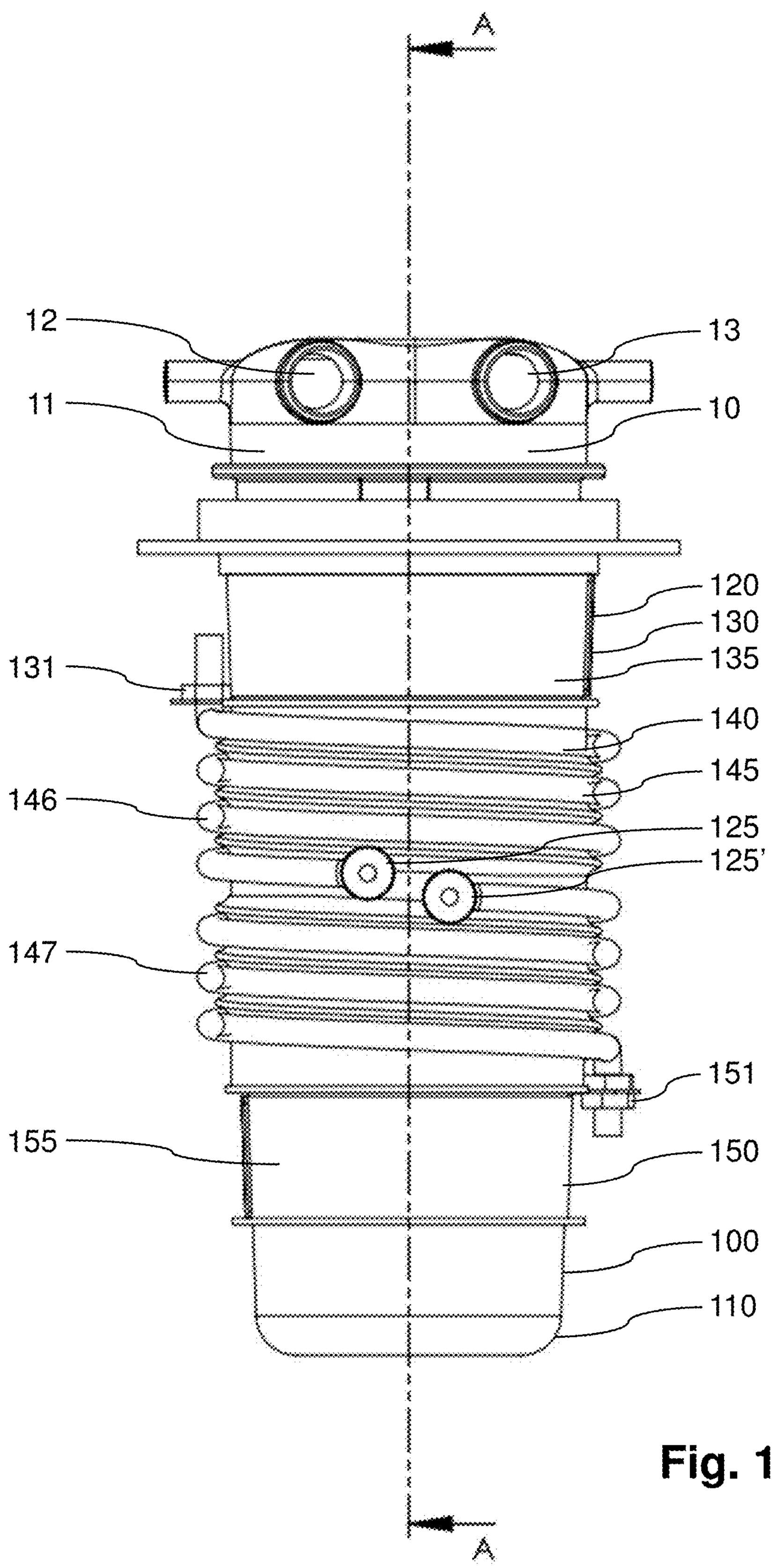
FIG. 1 schematically shows a heating device.

FIG. 1 schematically shows a heating device 100. Arrow A and the line pointed at by the arrow A indicate the viewing direction and the cross-section shown in FIG. 2, respectively. The heating device comprises a holder 110 and an electrical circuit 120. The holder may have a beaker shape as shown. The holder may provide a housing. The holder in FIG. 1 is shown while holding a channel 10. The channel comprises a channel wall 11. The channel wall is arranged for conducting a fluid. Conducting a fluid typically means that the channel wall is impermeable to the fluid for conducting the fluid through the channel. The heating device heats the fluid conducted by the channel wall. Conducting a fluid typically means that the fluid is flowing from one end of the channel to the other end of the channel. The channel further may comprise a fluid inlet 12 and a fluid outlet 13.

The electrical circuit comprises a first conductive surface 135 or an inductor 140. The electrical circuit shown in FIG. 1 comprises a first conductive surface 135 for forming in use a first capacitor 130, an inductor 140 and a second conductive surface 155 for forming in use a second capacitor 150. The electrical circuit further comprises an electrical connector 125, 125'. The electrical connector is electrically coupled to the first conductive surface, the second conductive surface and the inductor. Further, the electrical connector is couplable to a power source. The power source provides a quasi-static AC power to the electrical circuit at an operating frequency.

The first capacitor comprises a first conductive surface 135. The first conductive surface is arranged as one of the conductive surfaces of the first capacitor. The first conductive surface annularly surrounds the channel during use. The first conductive surface is typically ring shaped where the channel during use fits in. The other conductive surface of the first capacitor is formed by the fluid in the channel opposite the first conductive surface. The first conductive surface and the fluid opposite the first conductive surface are separated by at least the channel wall. They may further be separated by a wall from the holder. They may further be separated by an air gap, typically between the wall from the holder and the channel wall. The electrical circuit may comprise a first capacitor connector 131. The first capacitor connector electrically couples the first conductive surface to the inductor.

The second capacitor comprises a first conductive surface 155. The second conductive surface is arranged as one of the conductive surfaces of the second capacitor. The second conductive surface annularly surrounds the channel during use. The second conductive surface is typically ring shaped where the channel during use fits in. The other conductive surface of the second capacitor is formed by the fluid in the channel opposite the second conductive surface. The second conductive surface and the fluid opposite the second conductive surface are separated by at least the channel wall. They may further be separated by a wall from the holder. They may further be separated by an air gap, typically between the wall from the holder and the channel wall. The electrical circuit may comprise a second capacitor connector 151. The second capacitor connector electrically couples the second conductive surface to the inductor.

The inductor 140 may comprise an upper inductor half 146 and a lower inductor half 147. On one end, the upper inductor half is electrically coupled to the electrical connector 125. From this end the upper inductor half may spiral upwards around the channel wall. On the other end, the first capacitor connector electrically couples the upper inductor half to the first conductive surface. On one end, the lower inductor half is electrically coupled to the other electrical connector 125'. From this end the lower inductor half may spiral downwards around the channel wall. On the other end, the second capacitor connector electrically couples the lower inductor half to the second conductive surface.

FIG. 2 schematically shows a cross-section of a heating device 100 and the channel 10 also shown in FIG. 1. The cross-section is along the line pointed at by arrow A as shown in FIG. 1.

The holder may comprise grooves 111. The windings of the inductor run in the grooves, such that the distance between the winding and the fluid is reduced. This reduction causes more of the induced magnetic field and thus more of the inductively coupled current to be introduced in the fluid. The grooves further simplify the manufacturing, especially placing the windings of the inductor at the right location.

The holder may comprise recesses 112, 112'. The first conductive surface is arranged in the first recess 112. The second conductive surface is arranged in the second recess 112'. The recesses cause the respective conductive surfaces to be arranged closer to the fluid in the channel for increasing the capacitively coupled currents.

The tapered shape of the holder and the channel advantageously snugly fit into each other for reducing or even preventing an airgap between the holder and the channel. Reducing the airgap increases the effectivity of the capacitors and the inductor. The tapered shape further provides that the channel is easily placed in the holder. The holder may be a beaker as shown in FIGS. 1 and 2. The beaker having the channel placed inside the beaker may have a beaker space 113. The beaker space may have a low pressure compared to the environment. This low pressure may prevent or make it difficult to remove the channel from the beaker. The beaker may have a small hole for allowing air through from the outside to the beaker space. The hole is typically such small that air may pass through while fluid at least under atmospheric pressure cannot. The small hole allows air to fill the beaker space such that an under pressure is prevented and the channel is advantageously easily removable. Alternatively, the holder and/or the beaker may comprise a groove on the inside running along the length of the channel from the beaker space at the bottom of the beaker to the beaker opening at the top. The groove has the same advantageous effect as the small hole. Alternatively, channel may comprise a groove on the outside running along the length of the channel, when arranged in the holder or beaker, from the beaker space at the bottom of the beaker to the beaker opening at the top. The groove has the same advantageous effect as the small hole.

Figure 3:
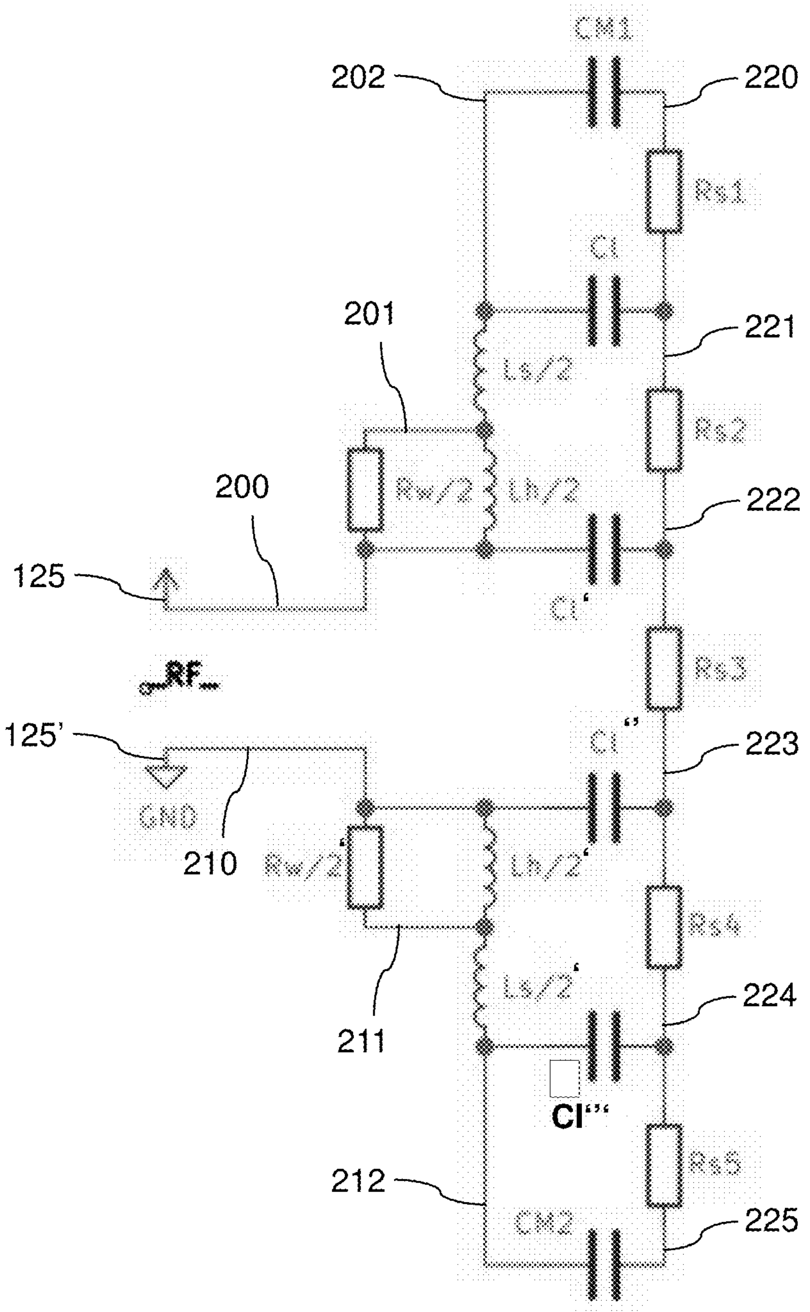
FIG. 3 schematically shows an electrical circuit of a heating device.

FIG. 3 schematically shows an electrical circuit 120 of a heating device 100. The electrical circuit may be a schematic representation of the electrical circuit of the heating device shown in FIGS. 1 and/or 2.

The electrical circuit comprises a positive connector 125 and a negative connector 125'. The electrical circuit further comprises at least a first conductive surface for forming in use a first capacitor 130, CM1, and an inductor L1, 140.

The electrical circuit further comprises a second conductive surface for forming in use a second capacitor CM2, 150. The inductor L1, 140 may comprise an upper inductor half Lh/2, 146, and a lower inductor half Lh/2, 147. The electrical circuit is further modelled with parasitic capacitors Cl, Cl', Cl'' and Cl''', resistors Rw/2 and Rw/2', and parasitic inductor Ls/2 and Ls/2'. The resistors Rw/2 and Rw/2' may be seen as the eddy current resistance in the fluid. The resistance experienced by the first capacitively coupled current, and/or the second capacitively coupled current is modelled with resistors Rs1, Rs2, Rs3, Rs4, and Rs5.

The electrical circuit may comprise nodes 200, 201, 202, 210, 211, 212, 220, 221, 222, 223, 224 and 225. The node 200 connects positive electrical connector 125, the resistor Rw/2, the upper conductor half Lh/2, and parasitic capacitor Cl'. The node 201 connects the resistor Rw/2, the parasitic inductor Ls/2, and the upper conductor half Lh/2. The node 202 connects the first capacitor CM1, the parasitic capacitor Cl, and the parasitic inductor Ls/2. The node 210 connects negative electrical connector 125', the resistor Rw/2', the lower conductor half Lh/2', and parasitic capacitor Cl''. The node 211 connects the resistor Rw/2', the parasitic inductor Ls/2', and the lower conductor half Lh/2'. The node 212 connects the second capacitor CM2, the parasitic capacitor Cl''', and the parasitic inductor Ls/2'. The node 220 connects the first capacitor CM1, and the fluid resistance Rs1. The node 221 connects the fluid resistance Rs1, the fluid resistance Rs2, and the parasitic capacitor Cl. The node 222 connects the fluid resistance Rs2, the fluid resistance Rs3, and the parasitic capacitor Cl'. The node 223 connects the fluid resistance Rs3, the fluid resistance Rs4, and the parasitic capacitor Cl''. The node 224 connects the fluid resistance Rs4, the fluid resistance Rs5, and the parasitic capacitor Cl'''. The node 225 connects the fluid resistance Rs5, and the second capacitor CM2.

Experiments have shown that the parasitic capacitors, the parasitic inductors, and the resistors Rw/2 and Rw/2' may be neglected when calculating the resonance frequency and the Q-factor of the electrical circuit. The resonance frequency may be approximated with:

$$f_{res} = \frac{1}{2\pi\sqrt{LC_M}},$$

wherein fres is the resonance frequency, L the inductance of the inductor, and CM the capacitance of the first capacitor and the second capacitor. The Q-factor may be approximated with:

$$Q = \frac{1}{R_S}\sqrt{\frac{L}{C_M}},$$

wherein Q is the Q-factor, and RS fluid resistance over the distance between first capacitor and the second capacitor through the fluid.

Figure 4:
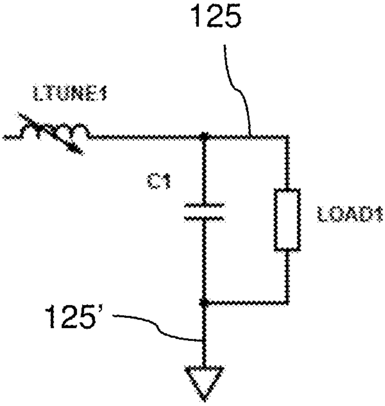
FIG. 4 schematically shows an electrical circuit of a heating device.

FIG. 4 schematically shows an electrical circuit 120 of a heating device 100. The electrical circuit comprises a positive connector 125 and a negative connector 125'. The electrical circuit further comprises a first conductive surface for forming in use a first capacitor Cl, and a fluid resistance LOAD1. The first capacitor and the fluid resistance are both coupled to the positive and negative connectors. Further, external to the electric circuit, between the power source and the electrical circuit, an inductive matchbox LTUNE1 may be arranged for matching the capacitance of the first capacitor Cl. This configuration advantageously simplifies the electrical circuit.

Figure 5:
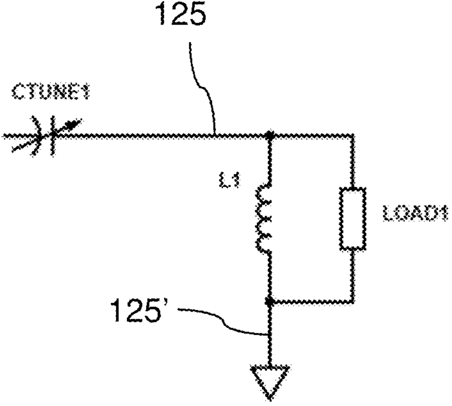
FIG. 5 schematically shows an electrical circuit of a heating device. The figures are purely diagrammatic and not drawn to scale. In the figures, elements which correspond to elements already described may have the same reference numerals.

FIG. 5 schematically shows an electrical circuit 120 of a heating device 100. The electrical circuit comprises a positive connector 125 and a negative connector 125'. The electrical circuit further comprises ain inductor L1, and a fluid resistance LOAD1. The inductor and the fluid resistance are both coupled to the positive and negative connectors. Further, external to the electric circuit, between the power source and the electrical circuit, a capacitive matchbox CTUNE1 may be arranged for matching the inductance of the inductor L1. This configuration advantageously simplifies the electrical circuit.

Examples, embodiments or optional features, whether indicated as non-limiting or not, are not to be understood as limiting the invention as claimed. It should be noted that the figures are purely diagrammatic and not drawn to scale. In the figures, elements which correspond to elements already described may have the same reference numerals.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" will be understood by, and be clear to, a person skilled in the art. The term "substantially" as well as "functionally" may also include embodiments with "entirely", "completely", "all", etc. Hence, in embodiments the adjective functionally may also be removed. When used, for instance in "functionally parallel", a skilled person will understand that the adjective "functionally" includes the term substantially as explained above. Functionally in particular is to be understood to include a configuration of features that allows these features to function as if the adjective "functionally" was not present. The term "functionally" is intended to cover variations in the feature to which it refers, and which variations are such that in the functional use of the feature, possibly in combination with other features it relates to in the invention, that combination of features is able to operate or function. For instance, if an antenna is functionally coupled or functionally connected to a communication device, received electromagnetic signals that are receives by the antenna can be used by the communication device. The word "functionally" as for instance used in "functionally parallel" is used to cover exactly parallel, but also the embodiments that are covered by the word "substantially" explained above. For instance, "functionally parallel" relates to embodiments that in operation function as if the parts are for instance parallel. This covers embodiments for which it is clear to a skilled person that it operates within its intended field of use as if it were parallel.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus or device comprising one or more of the characterising features described in the description and/or shown in the attached drawings. The invention further pertains to a method or process comprising one or more of the characterising features described in the description and/or shown in the attached drawings.

The various aspects discussed in this patent can be combined in order to provide additional advantages. Furthermore, some of the features can form the basis for one or more divisional applications.

The invention claimed is:

1. A heating device for heating a fluid used in a medical procedure, comprising:

a holder arranged for receiving a channel comprising a channel wall arranged for conducting the fluid; and an electrical circuit comprising:

a first conductive surface, arranged on the holder to annularly surround the channel in use and together with the channel wall and the fluid forming a first capacitor contributing to a capacitance of the electrical circuit, and for generating a first electrical field in the channel wall for introducing a first capacitively coupled current in the fluid;

a second conductive surface, arranged on the holder to annularly surround the channel in use and together with the channel wall and the fluid forming a second capacitor contributing to the capacitance of the electrical circuit, and for generating a second electrical field in the channel wall for introducing a second capacitively coupled current in the fluid; and an inductor contributing to an inductance of the electrical circuit, and arranged to the holder for generating a magnetic field for introducing an inductively coupled current in the fluid;

wherein the electrical circuit further comprises a connector electrically coupled to the first conductive surface, the second conductive surface and the inductor, and couplable to a power source providing a quasi-static AC power to the electrical circuit at an operating frequency; and wherein the fluid is selected from a perfusion fluid, a transfusion fluid, and an infusion fluid.

2. The heating device of claim 1, wherein the channel has a channel diameter and a longitudinal axis, and wherein one of:

a distance between a first conductive surface and a second conductive surface along the longitudinal axis is at least 1.0 times the channel diameter;

the distance between the first conductive surface and the second conductive surface along the longitudinal axis is at most 15 times the channel diameter; and the first conductive surface and the second conductive surface are arranged such that respectively the first capacitively coupled current in the fluid is substantially a first axial current and the second capacitively coupled current in the fluid is substantially a second axial current.

3. The heating device of claim 1, wherein the first conductive surface has a first truncated conical inner shape;

the second conductive surface has a second truncated conical inner shape; and the channel wall has at least a partly truncated conical shape for cooperating with the first conductive surface and the second conductive surface.

4. The heating device of claim 3, wherein the first truncated conical shape has a minimum diameter; the second truncated conical shape has a maximum diameter; and the minimum diameter is larger than the maximum diameter; or the first truncated conical shape and the second truncated conical shape are aligned to form one virtual conical shape; or the inductor is arranged for surrounding the channel.

5. The heating device of claim 1, wherein the channel comprises an input opening and an output opening; and the input opening and the output opening are arranged on the same side of the magnetic field, the inductor, the first electric field, the second electric field, the first conductive surface and/or the second conductive surface; or the second capacitively coupled current matches the first capacitively coupled current for introducing a capacitively coupled current in the fluid between the first conductive surface and the second conductive surface; or the first conductive surface and the second conductive surface are arranged on either side of the inductor, such that the first capacitively coupled current and the second capacitively coupled current flow through the magnetic field.

6. The heating device of claim 1, wherein the inductor is split in a first half and a second half; the first half of the inductor and the second half of the inductor are electrically coupled to the connector; an other side of the first half of the inductor is electrically coupled to the first conductive surface; and an other side of the second half of the inductor is electrically coupled to the second conductive surface; or in use the fluid has a resistivity per volume; the first conductive surface and the second conductive surface are spaced apart a coupling distance; and the coupling distance is selected such that the fluid resistivity between the first conductive surface and the second conductive surface substantially matches an output resistivity of the power source.

7. The heating device of claim 1, wherein the fluid is a perfusion fluid.

8. The heating device of claim 1, wherein the fluid is a transfusion fluid.

9. The heating device of claim 1, wherein the fluid is an infusion fluid.

10. The heating device of claim 1, wherein in use the channel wall at the first conductive surface has a first relative permittivity;

in use the first capacitor has a first capacitance depending on the first relative permittivity and a thickness of the channel wall local to the first conductive surface;

in use the channel wall at the second conductive surface has a second relative permittivity;

in use the second capacitor has a second capacitance depending on the second relative permittivity and a thickness of the channel wall local to the second conductive surface;

in use the fluid has a magnetic permeability;

the inductance is based on the magnetic permeability of the fluid;

the electrical circuit has a resistance based on the resistivity of the first capacitively coupled current, the inductively coupled current, and the second capacitively coupled current;

the electrical circuit has a reactance based on the capacitance and the inductance; and at the operating frequency, the ratio of the resistance and reactance is more than 2:1.

11. The heating device of claim 1, wherein the operating frequency is below 450 MHz;

the operating frequency is within a range of 433.05 MHz to 434.79 MHZ;

the operating frequency is within a range of 40.66 MHz to 40.7 MHz;

the operating frequency is within a range of 26.957 MHz to 27.283 MHZ;

the operating frequency is within a range of 13.553 MHz to 13.567 MHz; or the operating frequency is within a range of 6.765 to 6.795 MHz.

12. The heating device of claim 1, wherein in use the electrical circuit has a Q-factor based on the resistance, the capacitance, and the inductance;

the Q-factor is selected to accommodate for changes of the relative permittivity of the fluid and/or the magnetic permeability of the fluid over a temperature range of the fluid, and/or for changes of the relative permittivity of the fluid and/or the magnetic permeability of the fluid over different production batches;

the Q-factor is selected to accommodate in use for an air gap between the channel wall and the first conductive surface, the channel wall and the second conductive surface, of up to 100 μm; and the heating device comprises a reactance sensor for sensing a reactance of the electric circuit relative to a predefined reactance range for detecting a presence of a channel in the holder, the correct placing of the channel in the holder, a filling degree of the channel with fluid, and/or if a correct fluid is in the channel.

13. The heating device of claim 1, wherein the heating device is arranged for heating the fluid up under atmospheric pressure to a maximum temperature of 55 degrees Celsius;

the holder is arranged for replacing the channel;

the channel has an outer channel shape, and the holder has a tapered shape for receiving a tapered outer channel shape;

or in use the fluid has a magnetic permeability, in use the channel has a magnetic permeability, and the electric circuit is arranged for a fluid and a channel wherein the channel magnetic permeability is neglectable compared to the fluid magnetic permeability or in use the fluid has a relative permittivity, in use the channel has a relative permittivity, and the electric circuit is arranged for a fluid and a channel wherein the fluid relative permittivity is neglectable compared to the channel relative permittivity.

14. A heating assembly comprising:

the heating device of claim 1; and a channel for use in the heating device.

15. A flow sensor for measuring a flow of a fluid in a conduit, comprising:

the heating device of claim 1;

a first temperature sensor arranged upstream of the heating device for measuring a temperature of a fluid going into the heating device;

a second temperature sensor arranged downstream of the heating device for measuring a temperature of a fluid coming from the heating device; and an electrical power sensor arranged for measuring an electrical power inputted into the fluid by the heating device; and a controller arranged for:

receiving a first temperature from the first temperature sensor;

receiving a second temperature from the second temperature sensor;

receiving an electrical power value representing the electrical power inputted into the fluid;

retrieving a thermal capacity of the fluid;

retrieving a volumetric mass density of the fluid; and calculating the flow of the fluid based on the first temperature, the second temperature, the electrical power value, the thermal capacity, and the volumetric mass density.

16. The flow sensor of claim 15, wherein the step of calculating comprises the steps of:

subtracting the first temperature from the second temperature for providing a temperature change;

determining a received energy value based on a heat capacity and the temperature change;

dividing the electrical power value by the received energy for providing a mass per time unit of the flow; and dividing the mass of the flow by a volumetric mass density for providing the volume per time unit of the flow.

17. The flow sensor of claim 16, further comprising a first pressure sensor arranged for measuring a pressure of the fluid at the first temperature sensor; and a second pressure sensor arranged for measuring a pressure of the fluid at the second temperature sensor;

wherein the step of determining a received energy value is based on the pressure measurement of the first pressure sensor and the pressure measurement of the second pressure sensor to determine the pressure difference of the fluid at the first temperature sensor and at the second temperature sensor.

18. A temperature sensor for sensing a temperature of a fluid, comprising:

the heating device according to claim 1, wherein the fluid is conducted in the channel;

a power source providing a quasi-static AC power to the electrical circuit of the heating device, comprising:

a supply circuit for generating the operating frequency at a power output; and an impedance sensor for detecting an impedance of the electrical circuit; and a controller arranged for:

retrieving a function relating temperature and resonance frequency of the fluid;

determining a resonance frequency of the fluid in the channel based on changing the operating frequency; and determining the fluid temperature of the fluid in the channel based on the resonance frequency and the function relating temperature and resonance frequency.

19. The temperature sensor of claim 18, wherein the step of determining the resonance frequency comprises:

changing the operating frequency over a frequency range;

receiving impedance measurements, measured while changing the operating frequency, from the impedance sensor for detecting the impedance; and determining the resonance frequency based on an operating frequency with a lowest impedance.

20. The temperature sensor of claim 18, wherein the controller is arranged for lowering the power output of the supply circuit at least during determining the resonance frequency; and/or receiving a required fluid temperature; and setting a power output for heating the fluid to the required fluid temperature based on the required fluid temperature, wherein setting the power output is also based on one or more determined fluid temperatures.

* * * * *